United States Patent
Lang (10) Patent No.: US 7,883,548 B2
(45) Date of Patent: Feb. 8, 2011

(54) PROSTHETIC KNEE JOINT MECHANISM

(75) Inventor: Stephen Terry Lang, Hampshire (GB)

(73) Assignee: Chas. A. Blatchford & Sons Limited, Hampshire (GB)

( * ) Notice: Subject to any disclaimer, the term of this patent is extended or adjusted under 35 U.S.C. 154(b) by 1367 days.

(21) Appl. No.: 10/549,657

(22) PCT Filed: Mar. 12, 2004

(86) PCT No.: PCT/GB2004/001067

§ 371 (c)(1), (2), (4) Date: Sep. 16, 2005

(87) PCT Pub. No.: WO2004/082519

PCT Pub. Date: Sep. 30, 2004

(65) Prior Publication Data

US 2006/0224248 A1  Oct. 5, 2006

(30) Foreign Application Priority Data

Mar. 20, 2003  (GB) ................ 0306434.2

(51) Int. Cl.
*A61F 2/68* (2006.01)
(52) U.S. Cl. ...................................... 623/44
(58) Field of Classification Search ............ 623/26, 623/39–45, 57
See application file for complete search history.

(56) References Cited

U.S. PATENT DOCUMENTS 2,667,644 A  2/1954  Johnson
5,704,945 A *  1/1998  Wagner et al. ............... 623/44
6,113,642 A  9/2000  Petrofsky et al.
6,517,585 B1 *  2/2003  Zahedi et al. ................ 623/24

FOREIGN PATENT DOCUMENTS

| CA | 2134999 A | 5/1995 |
|---|---|---|
| DE | 9320853 U | 3/1995 |
| DE | 19506426 C | 11/1996 |
| EP | 1106884 A2 | 6/2001 |
| WO | WO 9908621 A2 * | 2/1999 |
| WO | WO 2004/045470 A1 | 6/2004 |

OTHER PUBLICATIONS

International Search Report for PCT Application No. PCT/GB2004/001067; Filed Mar. 12, 2004; Date of Completion Sep. 16, 2004; Date of Mailing Oct. 11, 2004.

* cited by examiner

*Primary Examiner*—William H. Matthews
(74) *Attorney, Agent, or Firm*—Alston & Bird LLP (57) ABSTRACT

A prosthetic knee joint mechanism has an hydraulic load-activated knee-stabilizing device for resisting joint flexion. A rotary piston (34) connected to one part of the mechanism is rotatable within a fluid-filled fluid displacement chamber (18) associated with another part of the mechanism to drive fluid through a fluid passage which contains a main valve (38) which restricts or allows joint flexion according to the position of a valve member within the valve. The valve member is movable towards an open position in response to fluid pressure in the fluid passage upstream of the valve member caused by application of a flexion torque to the knee joint mechanism, movement of the valve member in the direction of the open position being at least resisted by a valve control arrangement actuated by application of the wearer's weight. The weight-responsive valve control arrangement is preferably a weight-responsive pilot valve (32) for hydraulically resisting movement of the valve member of the main valve.

28 Claims, 4 Drawing Sheets

PROSTHETIC KNEE JOINT MECHANISM

BACKGROUND OF THE INVENTION

This invention relates to a prosthetic knee joint mechanism which includes a load-activated knee-stabilising device for restricting joint flexion.

It has long been known to include a stabilised knee as part of a prosthetic leg to achieve a natural looking gait, that is for the knee joint to resist flexion when under the load of part or all of the amputee's weight. Mechanical friction devices and hydraulic devices have been developed. In a known hydraulic stabilised knee joint mechanism, disclosed in Canadian Patent No. 2,134,999, resistance to flexion during the stance phase of the walking cycle and to extension during the swing phase is provided by restricting the movement of fluid between opposite sides of a rotary piston in a chamber filled with hydraulic fluid. In this mechanism the knee is locked by closing a fluid line by a valve interconnecting chamber parts on opposite sides of the piston using a valve member which moves when the application of the amputee's weight causes two resiliently connected parts of the mechanism to move relative to each other. The movement required to close the valve so to lock the knee is significant and creates a period of instability until the knee is locked. Also, overloading may damage the valve arrangement as it is directly operated.

BRIEF SUMMARY OF THE INVENTION

According to the first aspect of this invention, a prosthetic knee joint mechanism comprises first and second knee parts which are rotatable relative to each other in joint flexion and joint extension, and a load-activated knee-stabilising device for resisting joint flexion, the stabilising device comprising means defining a fluid-filled displacement chamber associated with the first knee part and a piston which is connected to the second knee part so as to be driven by rotation of the second knee part relative to the first knee part and which is so arranged within the chamber that it divides the chamber into first and second variable volume chamber parts which are interconnected by a fluid passage, the stabilising device further comprising a valve associated with the fluid passage and including a valve member which is movable between an open position in which fluid can flow through the passage to allow joint flexion and a stabilising position in which such fluid flow is at least restricted, wherein the valve member is movable towards its open position in response to fluid pressure in the interconnecting passage upstream of the valve member caused by application of a flexion torque to the knee joint mechanism, and wherein the stabilising device includes a weight-responsive valve control arrangement to at least resist movement of the valve member in the direction of its open position.

A feature of a preferred embodiment of the invention is its compactness, having the displacement chamber housed in the first knee part and being centred on an axis of relative rotation of the knee parts, the piston being in the form of a rotary piston which rotates with the second knee part. In the preferred embodiment, the valve comprises a main valve in which the valve member is movable in a fluid-filled valve cavity. The control arrangement for this valve comprises a weight-responsive pilot valve located in a secondary fluid passage which communicates with the above-mentioned valve cavity for hydraulically resisting or preventing movement of the valve member of the main valve in the direction of its open position. In fact, the main valve may be constructed as a shuttle valve having at least three ports which include an upstream port communicating with one of the variable volume chamber parts, a downstream port communicating with the other variable volume chamber part, and a control port. The upstream port opens into the valve cavity on one side of the valve member. The downstream port is located in the wall of the cavity so that it is fully or partially covered by the valve member in the stabilising position and is in communication with the upstream port when the valve member is in its open position. The control port opens into the valve cavity on the other side of the valve member from the upstream port and also forms part of the secondary passage.

In the preferred embodiment, the main valve has a bleed passage which interconnects the portions of the main valve cavity on opposite sides of the valve member; i.e. it effectively interconnects the upstream port and the control port. This bleed passage is conveniently located in the valve member of the main valve. The mechanism can be so arranged that the secondary fluid passage provides communication between the valve cavity of the main valve and the part of the fluid displacement chamber which increases in volume with joint flexion.

The main valve member is preferably resiliently biased towards its stabilising position. The yield of the knee joint may be adjusted by including a yield adjuster which forms an adjustable stop defining the stabilising position of the valve member. This may take the form of a needle stop which is arranged partially to close the bleed passage when the valve member is in its stabilising position. The variable yield under load allows a suitable setting to be found to enable the amputee to descend stairs leg-over-leg.

In a preferred embodiment of the invention the first knee part is configured as either a shin or thigh associated component and is divided into a pair of resiliently interconnected portions. One of these portions contains the fluid displacement chamber and the interconnected elements are arranged to execute a weight-responsive relative movement. The pilot valve is arranged in the first knee part so that it opens and closes in response to the relative movement of the resiliently connected portions of the knee mechanism, in particular closing to prevent movement of the shuttle valve member towards its open position during flexion, preferably by removing the force causing such movement during flexion. When weight is applied to the knee joint, the two elements of the first part of the knee mechanism move relative to each other, and the pilot valve responds. As a result, pressure in the secondary fluid passage changes so as to restrain the main valve member from moving to its open position when a flexion moment is applied. The primary passage between the two parts of the chamber containing the piston is restricted by the main valve member, restricting the movement of the piston. Hence, the movement of the two parts of the knee relative to each other is also restricted and the knee is stabilised.

According to another aspect of the invention, a prosthetic knee joint mechanism comprises a rotary piston in a fluid-filled displacement chamber, the mechanism being arranged such that the piston and the chamber resist joint flexion in response to weight activation, wherein the mechanism includes: a valve associated with a fluid passage interconnecting parts of the chamber on opposite sides of the piston, the valve having a valve member movable in response to upstream fluid pressure in the passage from a stabilising position, in which fluid flow in the passage is restricted, to an open position, in which fluid is allowed to flow in the passage more freely; and a weight-responsive valve control arrangement to resist movement of the valve member in the direction of its open position thereby to cause the mechanism to resist flexion.

The invention also includes a prosthetic knee joint mechanism comprising first and second knee parts which are rotatable relative to each other about an axis of rotation in joint flexion and joint extension, and a load-activated knee-stabilising device for resisting joint flexion, the stabilising device comprising means defining a fluid-filled displacement chamber associated with the first knee part and a piston which is centred on the knee axis of rotation and connected to the second knee part so as to be driven by relative rotation between the knee parts, and which is so arranged within the chamber that it divides the chamber into first and second variable volume chamber parts which are interconnected by a fluid passage, the stabilising device further comprising a valve associated with the fluid passage and including a valve member which is movable between an open position, in which fluid can flow through the passage to allow joint flexion, and a stabilising position, in which such fluid flow is at least restricted, wherein the valve member is movable towards its open position in response to a differential fluid pressure on opposite sides of the valve member caused by application of a flexion torque to the knee joint mechanism, and wherein the stabilising device includes a valve control arrangement substantially to eliminate the said differential pressure when the joint mechanism is loaded.

According to a further aspect of the invention, there is provided a lower limb prosthesis including a knee joint mechanism as set out above. One of the knee parts of the mechanism is preferably associated with or constituted by a shin component of the prosthesis and the other of the knee parts is associated with or constituted by the thigh component of the prosthesis. In particular, the said first and second knee parts may be associated with or constituted by the shin component and the thigh component respectively. Typically, but not necessarily, the axis of relative rotation of the first and second knee parts is the knee axis of rotation of the prosthesis.

An advantage of the mechanism described in this specification is that it is pilot operated in that a pilot or control arrangement controls the movement of a main valve member, hence the movement required to lock and release the knee is reduced. A near instant response is observed, providing a more stable knee. Another advantage is that it is adjustable in both the point at which stabilisation occurs and the extent of the lock stabilisation, i.e. in terms of locking the knee or allowing degrees of yield. The degree of yield may be altered to allow the amputee to descend stairs leg-over-leg or to descend steep slopes. Yet another advantage is that when unloaded the pilot arrangement, specifically the pilot valve in the preferred embodiment, is in contact with its controlling element, and that in weight activation such contact no longer exists, or the contact force decreases, so that overloading will not damage the pilot arrangement. In the unlocked position, free swing of the shin component is allowed in the flexion direction.

BRIEF DESCRIPTION OF THE DRAWINGS

The invention will now be described below by way of example with reference to the drawings, in to which.

DETAILED DESCRIPTION OF PREFERRED EMBODIMENTS

Referring to FIGS. 1 to 4, a prosthetic knee joint mechanism in accordance with the invention has an upper part 10 associated with a thigh component (not shown) of a limb prosthesis and a lower part 12 including the upper section of a shin component 14 of the prosthesis. The two joint mechanism parts, upper and lower, are pivotally interconnected, relative rotation occurring about a knee axis 16. The upper joint part 10 has a chassis 10A for receiving an alignment coupling (not shown), and associated medial and lateral flanges 10B which carry a axle 10C defining the knee axis (see FIG. 2). The axle is non-rotatably secured to the flanges 10B. The chassis 10A has posterior bushes 10AA for pivotal connection of a swing phase control unit (not shown). This unit typically takes the form of a pneumatic piston and cylinder assembly connected at one end to a pin housed in the bushes 10AA and at its other end to the shin component 14

The lower part 12 of the joint mechanism is in two main portions. One of the portions comprises a housing 12A containing an hydraulic chamber 18. Housing 12A has side plates 12AA (FIG. 2) and rotates on bearings 13 on the axle 10C. Housing 12A is also resiliently and pivotally connected to the upper section of the shin component 14 by a spindle 20 housed in medial and lateral side walls 14A of the shin component 14 (see FIG. 3). Spindle 20 defines a weight-sensing pivot axis 22 spaced from the knee axis of rotation 16 in the anterior-posterior direction. In this embodiment, the weight-sensing axis 22 is on the anterior side of the knee axis 16. Limited relative rotation of the housing 12A in the shin component 14 is governed by a resilient interconnection between the housing 12A and the shin component 14 in the form of an anteriorly extending plunger 24 pivotally mounted on a downwardly depending flange 12AB of the housing 12A, and slidably received in a bush 26 which is threaded in an anterior wall 14B of the shin component 14 (see FIG. 1) so as to be adjustable in position. Located between a posterior flange 24A on the plunger 24 and the posterior face of the adjustable bush 26 is a weight-sensing spring 28, here in the form of a stack of conical spring washers encircling plunger 24.

Figure 4:
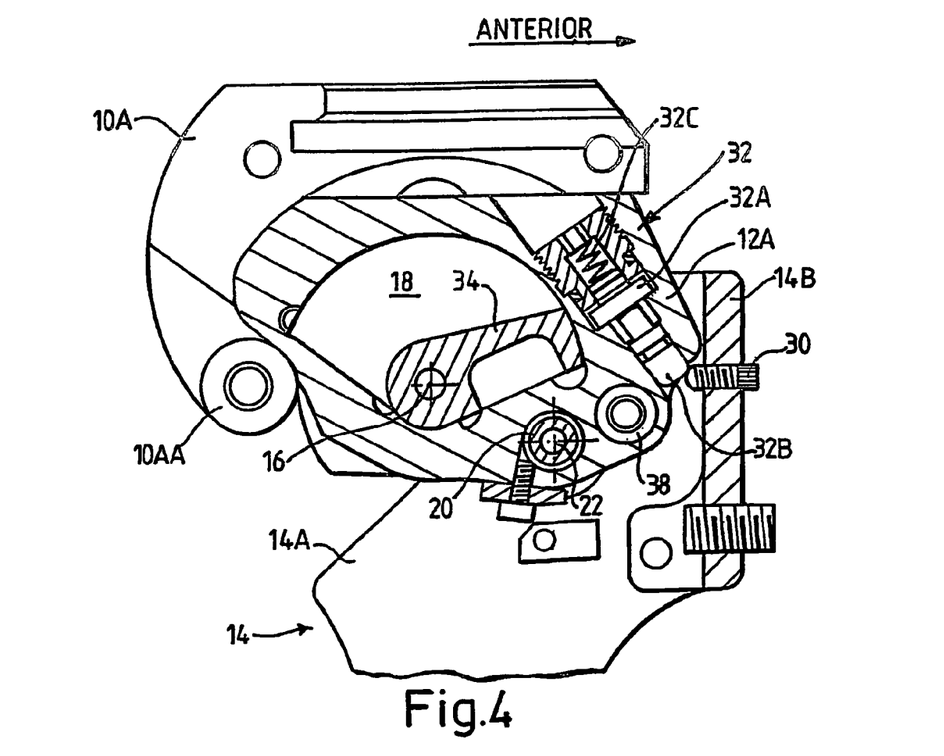
FIG. 4 is a second anterior-posterior cross-section of the mechanism in the plane indicated by 4-4 in FIG. 3.

Referring to FIG. 4, clockwise rotation of the housing 12A relative to the shin component 14 about the weight-sensing axis 22 causes abutment of a sensitivity adjusting element in the form of a grub screw 30 threaded in the anterior wall 14B of the shin component 14 against a control element in the housing 12A. This control element takes the form of a button 32B constituting an exposed anterior end of a pilot valve member 32A slidably housed in a pilot valve cavity to form a pilot valve 32, which will be described in more detail below. Pilot valve member 32A is resiliently outwardly biased by an internal valve closure spring 32C towards a position in which the valve is closed. The maximum extent of rotation of the shin component 14 about axis 22 in the direction of knee extension is limited by a final stop (not shown) on the housing 12A.

The hydraulic chamber 18 has a cross-section in the form of a sector of a circle centred on the knee axis 16. Housed sealingly within the chamber 18 is a rotary piston in the form of a vane 34 which is rotationally fixed with respect to axle 10C. Indeed, in this embodiment vane 34 is integral with axle 10C. When the knee mechanism is in the fully extended state, i.e. corresponding to full extension of the knee, the vane 34 is near its clockwise limit of rotation in the chamber 18, as it appears in FIGS. 1 and 4. As the knee is flexed, the vane sweeps around the chamber 18, displacing hydraulic fluid in a manner to be described below.

Weight-sensing occurs as a result of relative movement of the housing 12A and the shin component 14 about weight-sensing axis 22. Depending on the position of the ground reaction vector from the prosthetic foot (not shown) relative to the weight-sensing axis 22, application of the amputee's weight to the prosthesis gives rise to an anticlockwise moment on the housing 12A as viewed in FIGS. 1 and 4, tending to compress the spring 28, the plunger 24 moving anteriorly in bush 26. As a result, the housing 12A in the region of the pilot valve button 32B moves away from the grub screw element 30 in the anterior wall 14B of the shin component 14, and the pilot valve member 32A slides in its cavity in the housing 12A under the influence of the pilot valve closure spring 32C, thereby tending to close the pilot valve 32. Removal of the weight-responsive moment on the housing 12A allows the housing 12A to return to its unloaded position owing to the biasing force applied by spring 28.

In this embodiment of the invention, the pilot valve 32 has a central axis lying in a normally vertical anterior-posterior plane. Also housed in housing 12A is a main valve 38 which forms part of a primary passage interconnecting the two variable volume parts of the hydraulic chamber 18 which are separated from each other by the vane 34. This main valve 38 has an axis running in the medial-lateral direction. The two variable volume parts of the chamber 18 are also interconnected by a non-return valve 40 in the housing 12A (see FIG. 1).

The manner in which the pilot valve is activated by a knee flexion moment is adjustable. On the one hand, the bush 26, which forms a stop for the spring 28, is threaded in anterior wall 14B of the shin component 14 so that preloading of the spring 28 when no load is applied can be adjusted. This means that the stiffness of the weight-responsive resilient movement of the housing 12A relative to the shin component 14 can be adjusted depending on the weight of the amputee and his or her gait characteristics. This manifests itself as resilience tending to bias the joint towards full extension. On the other hand, sensitivity of operation of the pilot valve 32 is adjusted by screwing grub screw element 30 in or out. In effect, the adjustment of the grub screw 30 alters the amount of weight-responsive deflection of the housing 12A relative to the shin component 14 required to close the pilot valve 32, and also the point at which the pilot valve opens as weight is removed. Accordingly, the screw element 30 adjusts the timing of the locking and release of the knee mechanism, as will be appreciated from the description which follows.

Details of the main valve 38, the pilot valve 32 and their interaction will now be described with reference to FIGS. 5, 6A and 6B.

Figure 5:
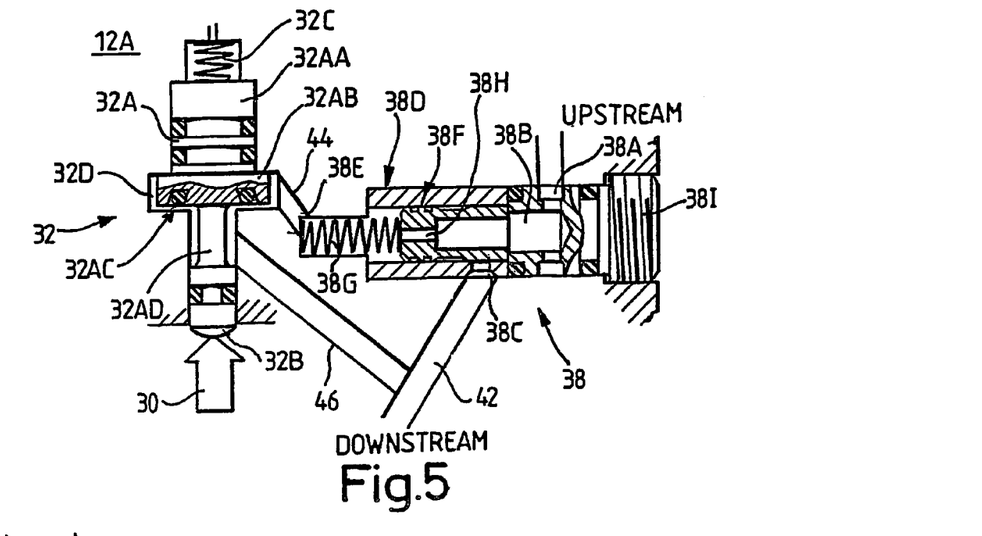
FIG. 5 is a schematic diagram of an hydraulic system of the mechanism showing primary and secondary fluid passages.

Referring to FIG. 5, the main valve 38 is a shuttle valve having an upstream port 38A opening into one end of a valve cavity 38B, and a downstream port 38C in a sidewall formed, in this case, by a honed sleeve 38D. Cavity 38B extends axially of the valve to a control port 38E at the opposite end of the cavity from the upstream port 38A. Housed in the cavity 38B is a cylindrical shuttle valve member 38F which slides in a sealed manner in the sleeve 38D and is biased by an internal spring 38G against a shoulder in the cavity 38B. It will be seen that the shuttle member divides the cavity 38B into two portions, one communicating with the upstream port 38A and the other communicating with the control port 38E. These two cavity parts are interconnected by a bleed passage 38H which, in this case, is an orifice formed by a narrow axial bore 38H in the shuttle valve member 38F. A threaded plug 38I closes off the valve cavity 38B.

Shuttle valve 38 lies in a primary passage 42 in the housing 12A (see FIG. 1) interconnecting the variable volume parts of hydraulic chamber 18. The upstream port is "upstream" in the sense that it is upstream when the knee joint flexes.

The pilot valve 32 has already been briefly described with reference to FIG. 4. As will be seen from FIG. 5, the pilot valve member has four main parts as follows. Firstly the valve member 32A has a wide cylindrical body portion 32AA housed in a first cylindrical bore in the housing 12A. Adjacent body portion 32AA is a flange portion 32AB having an outwardly directed sealing wall with an annular sealing ring 32AC lying in a plane perpendicular to the pilot valve axis. Projecting axially from this axially directed sealing face is a narrow stem 32AD carrying at its end the pilot valve button 32B referred to above. The material of the housing 12A surrounding the flange 32AB and the stem 32AD is bored to provide an annular pilot valve cavity spaced laterally of both such portions 32AB and 32AD, and an annular shoulder against which the sealing ring 32AC abuts when the valve member 32A is allowed to move outwardly under the influence of closure spring 32C (when weight is allied to the knee mechanism as described above with reference to FIGS. 1 and 4).

The pilot valve forms part of a secondary passage between the control port 38E of the main valve 38 and the downstream port 38C of the main valve 38, a bore 44 being formed in the body of the housing 12A to interconnect the main valve control port 38E with the pilot valve cavity 32D on one side of the sealing member 32AC, and another bore 46 opening into the pilot valve cavity 32D adjacent the stem 32AD, i.e. on the opposite side of the sealing member 32AC.

Figures 6A, 6B:
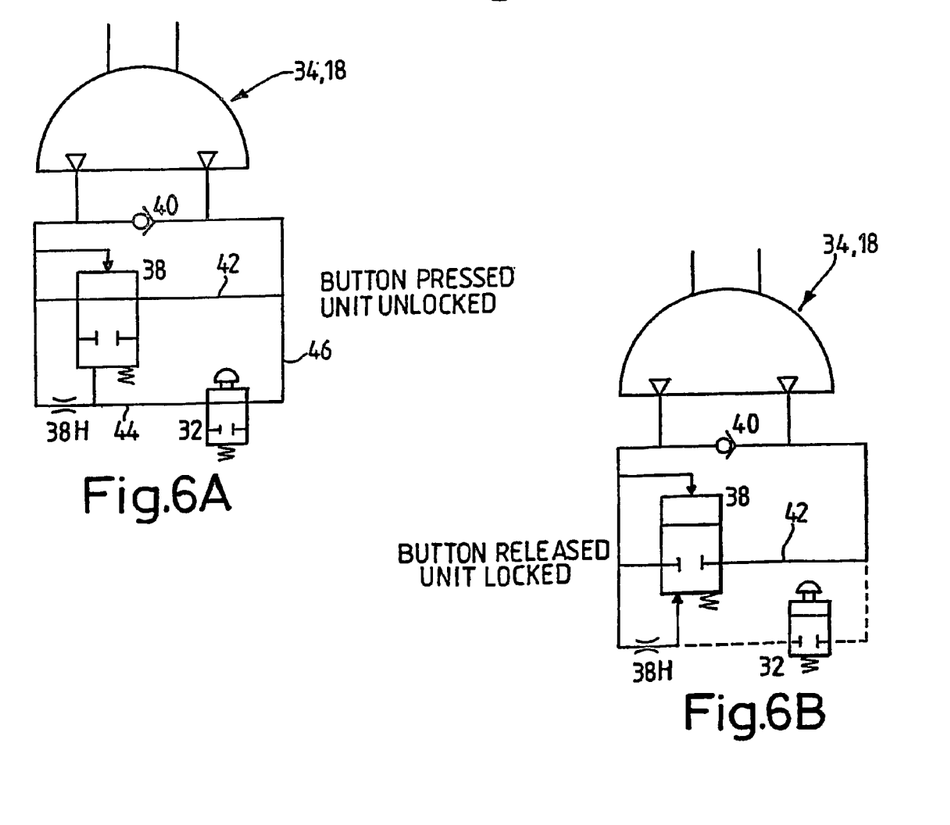
FIGS. 6A and 6B are hydraulic circuit diagrams of the mechanism.

The disposition of the main valve 38 and pilot valve 32 in the hydraulic circuit of the knee joint mechanism is more clearly shown in FIGS. 6A and 6B. Bleed passage 38H appears as a restricted flow passage between the upstream side of the main valve 38 and the secondary passage 44, 46 on the control port side of the main valve 38. The disposition of the non-return valve 40 is also shown.

Operation of the valve is generally as follows. Without weight-activation, flexion of the knee joint causes hydraulic fluid to be driven by the vane 34 from one variable volume part of the chamber 18 through the upstream and downstream ports 38A and 38C to the other variable volume part of the chamber 18. If the unit is weight-activated either during or prior to flexion of the knee joint, the shuttle valve interrupts the flow of fluid between the two chambers causing the knee to lock (i.e. to be stabilised). During extension of the knee joint, the vane 34 forces the fluid in the opposite direction via the non-return valve 40 (FIGS. 6A and 6B) to ensure free swing in the extension direction at all times subject, of course, to any resistance imposed by a swing phase control unit attached between the first and second parts of the mechanism.

In the swing phase, prior to rotation at the knee joint, the housing 12A is held in such a position by the spring 28 (see FIG. 1) as to maintain the pilot valve 32 open, providing communication between the control port 38E of the main valve 38 and the downstream part of the primary passage between the two variable volume parts of the chamber 18. At this time, the shuttle valve member 38F is urged against the shoulder in the main valve cavity 38B by the spring force of spring 38G, covering the downstream port 38C, as shown in FIG. 5.

Flexion of the knee joint causes an increase in pressure upstream of the shuttle valve 38. Bearing in mind that the control port is open to the downstream side so long as pilot valve 32 is open, the differential pressure across the shuttle valve 38 causes the valve member to slide away from the shoulder stop in cavity 38B, compressing the spring 38G and, thereby, uncovering the downstream port 38C. As a result, fluid may flow from the upstream port 38A to the downstream port 38C, and the shin component 14 may freely swing.

However, when weight is applied to the limb in such a way as to produce a flexion moment within the knee mechanism sufficient to rotate the housing 12A against the spring 28 (FIG. 1), button 32B of the pilot valve 32 is allowed to move outwardly in the housing 12A, the pilot valve thereby closing under the force of its closure spring 32C. The control port 38E of the shuttle valve 38 is now closed off and the secondary passage interrupted. Pressure on the control port side of the shuttle member 38F is then equalised with that at the upstream port 38A owing to fluid flow through the bleed passage 38H. The previously described differential pressure across the valve member 38F is thereby removed. Should weight be applied prior to flexion of the knee joint, the shuttle valve member 38F is prevented from moving away from its closed position, i.e. with downstream port 38C closed. Should weight be applied during flexion of the knee (for instance when the amputee stumbles), the shuttle valve member 38F is returned from an open position to its closed position by the spring force of spring 38G. In the closed position of the shuttle valve member 38F, the downstream port 38C is cut off from the upstream port 38A, thereby interrupting the flow of fluid between the two variable volume parts of the chamber 18, causing the knee to stabilise.

Figure 1:
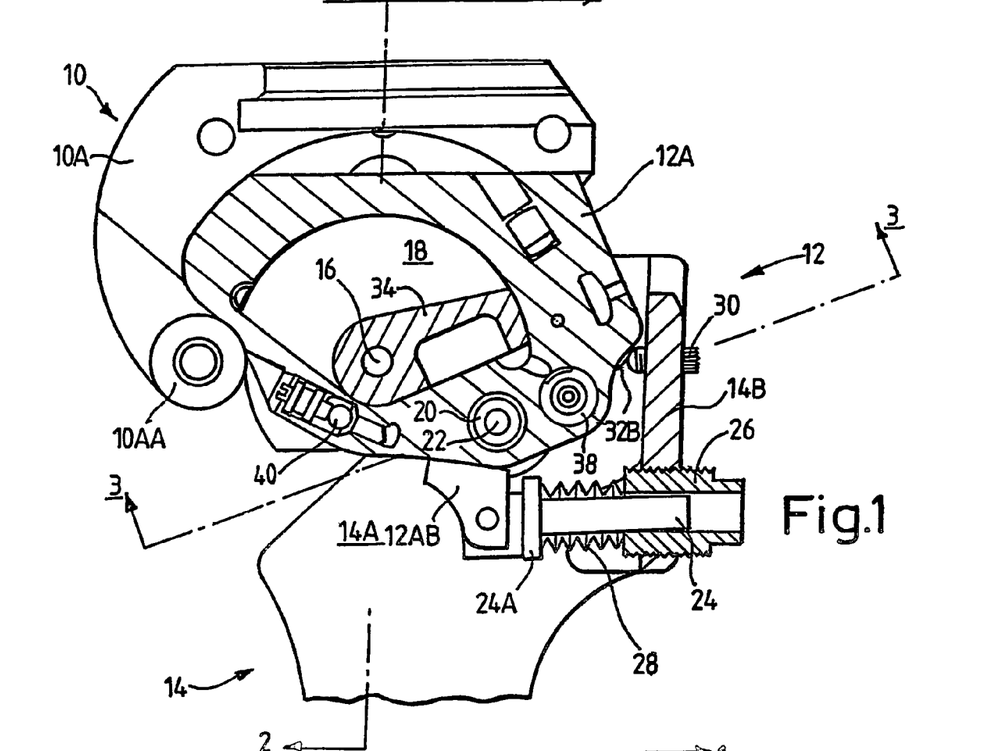
FIG. 1 is a cross-section of a knee-mechanism in accordance with the invention, the cross-section being in a central anterior-posterior plane.
Figure 2:
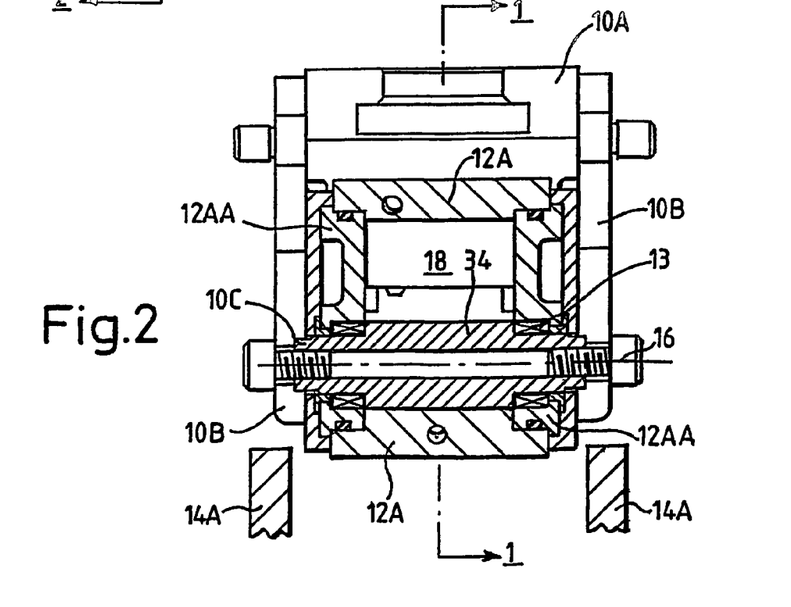
FIG. 2 is a cross-section of the mechanism in a generally vertical medial-lateral plane through the knee axis of rotation, the plane being indicated by the line 2-2 in FIG. 1.

It will be understood, then, that the knee mechanism is locked or stabilised during the stance phase of the walking gait cycle, when the flexion moment caused by the ground reaction vector overcomes the restoring force of the spring 28 (FIG. 1). When that flexion moment is insufficient to overcome the spring force, the housing 12A rotates about weight-sensing pivot axis 22, forcing the pilot valve 32 to open. This, in turn, causes the pressure on the control port side of the shuttle valve member 38F to drop and, therefore, the shuttle valve member 38F slides to its open position due to upstream pressure in the upstream port 38A, allowing fluid to flow once again between the two parts of the hydraulic chambers 18.

FIG. 6A illustrates the state of the hydraulic circuit when the knee joint is being flexed without weight application. FIG. 6B shows the hydraulic state when a flexion moment is applied when the mechanism is weight-activated. As described above, when weight-activated, the pilot valve 32 is closed, removing the differential pressure across the shuttle valve 38 so that the latter closes.

Figure 3:
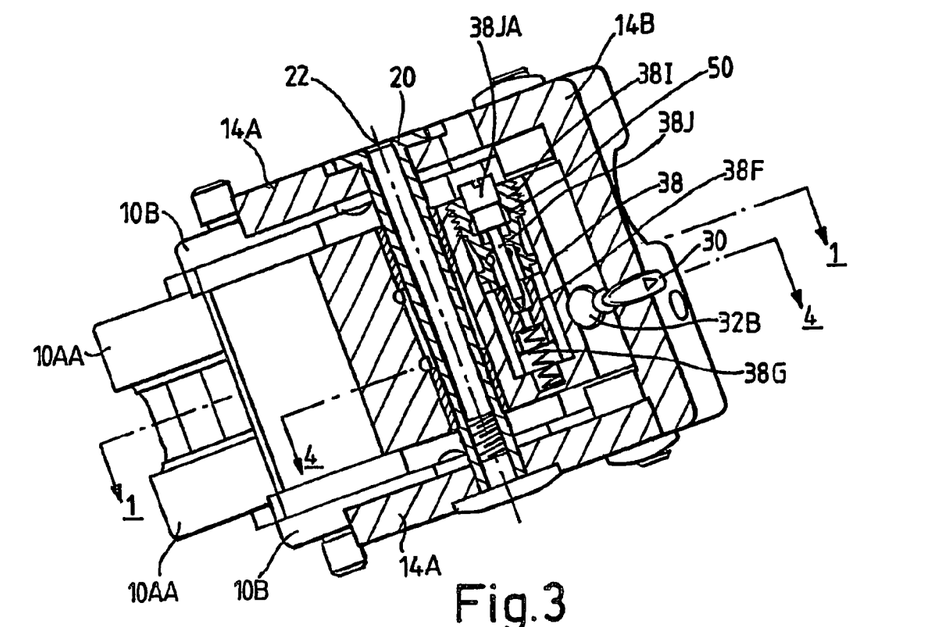
FIG. 3 is a cross-section of the mechanism taken in the inclined medial-lateral plane 3-3 in FIG. 1.

The arrangement of the shuttle valve shown in FIG. 5 is simplified. In the preferred shuttle valve 38, means for adjusting the stabilising action of the mechanism is provided in the form of a yield adjuster 50, as shown in FIG. 3. In this preferred embodiment, the plug 38I has a threaded axial bore which receives an axial needle member 38J having a threaded screw head 38JA. The needle member 38J extends through the upstream part of the main valve cavity 38B to a free end which abuts the shuttle valve member 38F when it is in its closed position. Advantageously, the needle 38J has a tapered end which is received in the bleed passage 38H. Depending, therefore, on the position of the needle member 38J, equalisation of the pressure on opposite sides of the shuttle valve member when the pilot valve 32 is closed does not cause complete covering of the downstream port 38C. This variable leak has the effect of an adjustable yield instead of full lock. It follows that if the amputee wishes to descend stairs "leg-over-leg", the shuttle valve closed position can be set to produce the appropriate level of support. This support may also be used by the amputee for descending steep slopes.

The tapered end of the needle member 38J is received in the bleed passage 38H (see FIG. 5) of the shuttle valve member 38F when the latter it is its closed position. The action of the tapered end entering the bleed passage hydraulically damps the movement of the valve member 38F, largely preventing any significant noise associated with valve closure.

A particular property of the pilot valve 32 described above with reference to FIG. 5 is that the sealing area, determined by the annular seal 32AC and/or the associated parts of the pilot valve member 32A, is smaller than the sealing area of the wide valve body portion 32AA, with the result that a very high upstream pressure transmitted through the bleed passage 38H in the main valve 38 causes the pilot valve to open against the spring 32C. The pilot valve 32, therefore, acts as an over-pressure release valve to prevent hydraulic pressure damaging the mechanism. In effect, by using different sealing areas for the pilot valve closed position, the valve can be made to open at a predetermined limiting pressure. The effect felt by the amputee is a yielding of the knee when loaded excessively.

Figure 7:
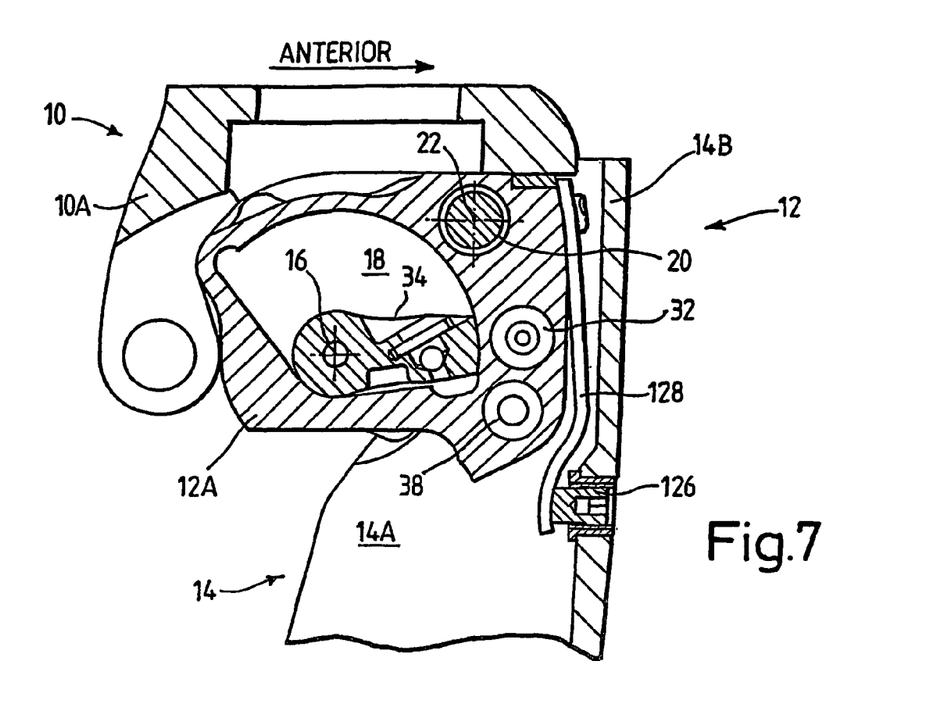
FIG. 7 is a cross-section of an alternative knee mechanism in accordance with the invention, the cross-section being in a central anterior-posterior plane.

Parts of an alternative knee mechanism in accordance with the invention are shown in cross-section in FIG. 7. The main differences are the adoption of a leaf spring 128 to bias the vane housing 12A towards its unloaded position relative to the shin component 14, and the medial-lateral disposition of the pilot valve 32 in the housing 12A, the exposed end of the pilot valve stem 32AD projecting from a side face 12AS of the housing 12A to abut an adjustable projection mounted in the adjacent sidewall 14A of the shin component 14, as shown in the detail of FIG. 8.

Details of this alternative embodiment will be described only where it differs from the embodiment of FIGS. 1 to 5 but, to aid understanding, the same reference numerals are used in FIGS. 7 and 8 as in FIGS. 1 to 5 where the two embodiments have corresponding parts.

Referring to FIG. 7, the leaf spring 128 is fixed at a proximal end to an anterior face of the housing 12A, and extends distally behind the anterior wall 14B of the shin component 14 to abut an adjustable abutnent member 126 threaded in the anterior shin component wall 14B. Leaf spring 128 biases the shin component 14 about weight-sensing axis 22 in the direction of knee extension. As in the case of the bush 26 of the embodiment of FIGS. 1 to 5, the adjustment member 126 in this alternative embodiment, being threaded in the anterior wall 14B of the shin component 14, can be adjusted to alter the preloading of the spring 128 so as to define the stiffness of the connection between the housing 12A and the shin component 14.

Figure 8:
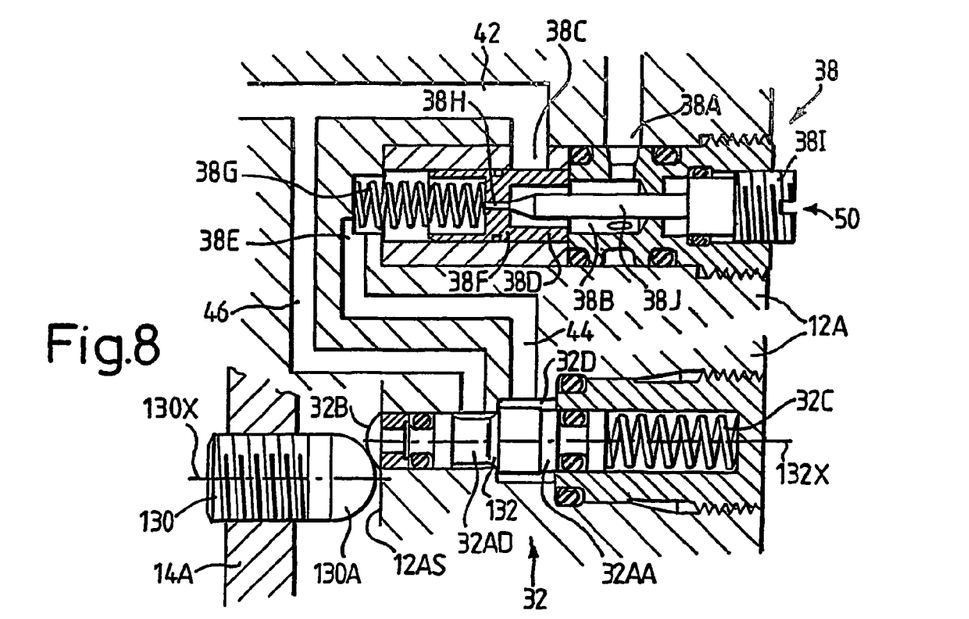
FIG. 8 is a diagrammatic cross-sectional detail of part of the mechanism of FIG. 7, the cross-section being in a medial lateral plane.

Referring to FIG. 8, the exposed end portion 32B of the pilot valve stem 32AD is generally in registry with a domed inner end 130A of the adjustable projection 130, button 32B sliding over domed end 130A as the shin component 14 moves with respect to the vane housing 12A. More specifically, subject to the ground reaction vector from the prosthetic foot (not shown) passing to the posterior of the weight sensing axis 22, when the amputee applies weight to the prosthesis sufficiently to cause deflection of the vane housing against the biasing force of the leaf spring 128, the axis 132X of the pilot valve button 32B moves away from the axis 130X of the adjustment member 130 so that the pilot valve closure spring 32C causes the pilot valve stem 32AD to move to the position in which the pilot valve 32 is closed. This is the position of the pilot valve stem 32AD shown in FIG. 8. When the amputee's weight is removed, button 32B moves to a position more in registry with adjustment member 130, causing the pilot valve to open.

In this embodiment, sealing between the valve stem 32AD of the pilot valve 32 and the walls of the pilot valve cavity in the housing 12A occurs by direct contact between the valve stem 32AD and the cavity wall, in this case by abutment of a conical portion 132 of the valve stem 32AD with a coaxial annular shoulder in the cavity wall.

Overload protection of the hydraulic circuit is achieved as in the embodiment of FIGS. 1 to 5, in that the sealing diameter of that portion of the valve stem determining the pressure required to open the valve against the closure spring 32C is marginally larger than the diameter of the annular seal formed between the conical surface 132 of the valve stem 32AD and the wall of the pilot valve cavity 32D. The respective seals, i.e. of the wide valve body portion 32AA and the sealing surface 132 are on opposite sides of the valve cavity 32 with respect to the port formed by the secondary passage 44 where it opens into the cavity 32D.

The main valve 38 has a construction in this embodiment similar to that described above with reference to FIG. 3, in that it has a yield adjuster 50 with a needle member 38J in registry with the bleed hole 38H in the shuttle valve member 38F.

Use of a leaf spring 128, as shown, with its major cross-sectional axis in the medial-lateral direction, as well as the medial-lateral disposition of the pilot valve 32 and pilot valve axis 132X, results in a lighter and more compact mechanism compared with that of FIGS. 1 to 5, particularly in terms of its anterior extent relative to the knee axis 16.

Variations on the structure described above are possible. For instance, the knee part 10 may be integral with a thigh component of a lower limb prosthesis. The weight-responsive parts of the limb may be associated with the prosthetic thigh rather than the shin as shown. A notable feature of the mechanism is that the main valve member is normally in its closed position and is pushed open by the operating pressure resulting from knee joint flexion. Movement of the valve member towards the open position is a result of such pressure. Such movement is not possible when the control arrangement operates to prevent application of a differential pressure on opposite sides of the valve member. It is possible, however, to prevent movement of the main valve member mechanically rather than hydraulically. Allowing the main valve member to be pushed open by operating pressure has the advantage that the secondary control function can be brought about other than as a result of movement of the main valve member with the consequent advantage of minimal take-up movement before the fluid passage between opposite sides of the piston is interrupted and, in addition, precise adjustment.

The invention claimed is:

1. A prosthetic knee joint mechanism comprising first and second knee parts which are rotatable relative to each other in joint flexion and joint extension, and a load-activated knee-stabilizing device for resisting joint flexion during a stance phase of the walking gait cycle, the stabilizing device comprising means defining a fluid-filled fluid displacement chamber associated with the first knee part and a piston which is connected to the second knee part so as to be driven by rotation of the second knee part relative to the first knee part and which is so arranged within the chamber that it divides the chamber into first and second variable volume chamber parts which are interconnected by a fluid passage, the stabilizing device further comprising a valve associated with the fluid passage and including a valve member which is movable within a housing between a stabilizing position in which the valve member at least restricts fluid flow through the passage so as to resist joint flexion and an open position in which fluid can flow through the passage to allow joint flexion, wherein the valve member is movable towards its open position in response to fluid pressure in the interconnecting passage upstream of the valve member caused by application of a flexion torque to the knee joint mechanism, and wherein the stabilizing device includes a stance phase weight-responsive valve control arrangement which, in use, operates in response to patient loading to at least resist movement of the valve member in the direction of its open position thereby to cause the mechanism to resist joint flexion during the stance phase.

2. A mechanism according to claim 1, wherein the displacement chamber is in the first knee part and is centered on an axis of relative rotation of the first and second knee parts, and the piston is a rotary piston which rotates with the second knee part.

3. A mechanism according to claim 1, wherein said valve is a main valve in which the valve member is movable in a fluid-filled valve cavity of the main valve, and wherein the control arrangement comprises a weight-responsive pilot valve forming part of a secondary fluid passage which communicates with the valve cavity for hydraulically resisting movement of the valve member of the main valve in the direction of its open position.

4. A mechanism according to claim 3, wherein the main valve comprises a shuttle valve having an upstream port opening into the valve cavity on one side of the valve member, a downstream port located in a wall of the cavity so as to be at least partially covered by the valve member in its stabilizing position and in communication with the upstream port via the valve cavity when the valve member is in its open position, and a control port opening into the valve cavity on the other side of the valve member, the control port forming part of the secondary passage.

5. A mechanism according to claim 3, wherein the main valve includes a bleed passage interconnecting portions of the valve cavity on opposite sides of the valve member.

6. A mechanism according to claim 5, wherein the bleed passage is located in the valve member.

7. A mechanism according to claim 1, including means for biasing the valve member towards its stabilizing position.

8. A mechanism according to claim 7, wherein the biasing means comprises a spring.

9. A mechanism according to claim 5, including a yield adjuster in the form of an adjustable stop defining the stabilizing position of the valve member.

10. A mechanism according to claim 9, wherein the adjustable stop is arranged to close the bleed passage at least partially when the valve member is in its stabilizing position.

11. A mechanism according to claim 3, wherein the secondary fluid passage provides fluid communication between the valve cavity of the main valve and that part of the fluid displacement chamber which increases in volume with joint flexion.

12. A member according to claim 3, wherein the pilot valve includes a plunger spring-biased towards a closed position.

13. A mechanism according to claim 3, wherein the first knee part is configured as a shin-associated component or a thigh-associated component and is divided into a pair of resiliently interconnected elements one of which contains the fluid displacement chamber, the interconnected elements being arranged to execute a weight-responsive relative movement, and wherein the pilot valve is so arranged in the first knee part that it opens and closes in response to relative movement of the resiliently interconnected elements.

14. A lower limb prosthesis including a knee joint mechanism according to claim 1.

15. A prosthesis according to claim 14, wherein one of the knee parts is associated with or is constituted by a shin component of the prosthesis, and the other of the knee parts is associated with or is constituted by a thigh component of the prosthesis.

16. A prosthesis according to claim 15, wherein the first and second knee parts are associated with or constituted by the shin component and the thigh component respectively.

17. A prosthetic knee joint mechanism comprising a piston in a fluid-filled fluid displacement chamber, the mechanism being arranged such that the piston and the chamber resist joint flexion in response to weight activation, wherein the mechanism includes: a valve associated with a fluid passage interconnecting parts of the chamber on opposite sides of the piston, the valve having a valve member movable in response to upstream fluid pressure in the passage from a stabilizing position, in which fluid flow in the passage is restricted, to an open position, in which fluid is allowed to flow more freely; and a stance phase weight-responsive valve control arrangement which, in use, operates in response to patient loading to resist movement of the valve member in the direction of its open position thereby to cause the mechanism to resist flexion during the stance phase.

18. A mechanism according to claim 17, wherein the piston and the displacement chamber, which is of circular configuration, are centered on an axis of relative rotation of two parts of the mechanism which rotate relatively to each other in joint flexion.

19. A mechanism according to claim 17, wherein the valve control arrangement comprises a pilot valve in fluid communication with a fluid-filled valve cavity housing the valve member, the mechanism being configured such that the pilot valve closes in response to weight-activation thereby to prevent movement of the valve member in the direction of its open position.

20. A mechanism according to claim 19, wherein the valve in the interconnecting passage between opposite sides of the piston includes a bleed passage allowing restricted fluid flow between parts of the valve cavity on opposite respective sides of the valve member, the valve member being resiliently biased towards its stabilizing position.

21. A mechanism according to claim 19, comprising a shin-associated portion and a thigh-associated portion which rotate relatively to each other in joint flexion and joint extension, one of which portions is divided into resiliently interconnected parts arranged to execute a weight-sensing movement relative to each other, wherein the pilot valve is mechanically operable by such relative movement.

22. A prosthetic knee joint mechanism comprising first and second knee parts which are rotatable relative to each other about a knee axis of rotation in joint flexion and joint extension, and a load-activated knee-stabilizing device for resisting joint flexion during a stance phase of the walking gait cycle, the stabilizing device comprising means defining a fluid-filled displacement chamber associated with the first knee part and a piston which is centered on the knee axis of rotation and connected to the second knee part so as to be driven by relative rotation between the knee parts, and which is so arranged within the chamber that it divides the chamber into first and second variable volume chamber parts which are interconnected by a fluid passage, the stabilizing device further comprising a valve associated with the fluid passage and including a valve member which is movable between an open position in which fluid can flow through the passage to allow joint flexion and a stabilizing position in which such fluid flow is at least restricted, wherein the valve member is movable towards its open position in response to differential fluid pressure on opposite sides of the valve member caused by application of a flexion torque to the knee joint mechanism, and wherein the stabilizing device includes a valve control arrangement to substantially eliminate said differential pressure when, in use, the joint mechanism is loaded during the stance phase.

23. A mechanism according to claim 22, wherein the valve member is resiliently biased towards its stabilizing position.

24. A lower limb prosthesis having a shin component and a thigh component which are rotatable relatively to each other in joint flexion and joint extension, and including a knee joint mechanism as claimed in claim 17.

25. A prosthesis according to claim 24, wherein the piston and the displacement chamber, which is of circular configuration, are centered on an axis of relative rotation of two parts of the mechanism which rotate relatively to each other in joint flexion, wherein the shin and thigh components are rotatable relatively to each other about a fixed knee axis of rotation, and wherein one of the mechanism parts is associated with the shin component and the other of the knee mechanism parts is associated with the thigh component, the mechanism parts being rotatable relatively to each other about the knee axis of rotation.

26. A prosthesis according to claim 25, wherein the fluid displacement chamber is associated with the shin component and the piston is associated with the thigh component.

27. A prosthetic joint mechanism comprising first and second joint parts which are rotatable relative to each other in joint flexion and joint extension, and a joint-stabilizing device comprising means defining a fluid-filled fluid displacement chamber associated with the first joint part and a piston which is connected to the second joint part so as to be driven in the chamber by relative rotation of the joint parts, the stabilizing device including a hydraulic valve controlling the flow of fluid to and/or from the fluid displacement chamber; wherein the valve comprises a valve member which is movable between an open position and a closed position in a valve cavity in response to an external force on the valve member during a stance phase of the walking gait cycle, the cavity having an inlet port at least indirectly in communication with the fluid displacement chamber, and an outlet port which is closed by the valve member when in the closed position, the valve member being resiliently biased towards the closed position and having a piston part located in a bore which opens into the cavity on an opposite side of the cavity from the outlet port, and wherein the effective sealing area of the piston part in the bore is greater than the effective sealing area of the valve member at the outlet port, whereby the valve member is caused to move away from its closed position in the event of pressure in the cavity caused by an excessive flexion moment applied to the joint mechanism during the stance phase.

28. A joint mechanism according to claim 27, wherein the valve is a pilot valve arranged to control operation of a main hydraulic valve which is located in a primary hydraulic passage between parts of the fluid displacement chamber on respective opposite sides of the piston.

* * * * *

UNITED STATES PATENT AND TRADEMARK OFFICE
CERTIFICATE OF CORRECTION

| | | |
|---|---|---|
| PATENT NO. | : 7,883,548 B2 | Page 1 of 1 |
| APPLICATION NO. | : 10/549657 | |
| DATED | : February 8, 2011 | |
| INVENTOR(S) | : Lang | |

It is certified that error appears in the above-identified patent and that said Letters Patent is hereby corrected as shown below:

Column 8,
Line 50, "abutnent" should read --abutment--.

Column 9,
Line 25, "32" should read --32D--.

Signed and Sealed this
Fifth Day of July, 2011

David J. Kappos
*Director of the United States Patent and Trademark Office*